United States Patent [19]

Pentoney, Jr. et al.

[11] Patent Number: 5,675,155
[45] Date of Patent: Oct. 7, 1997

[54] MULTICAPILLARY FLUORESCENT DETECTION SYSTEM

[75] Inventors: Stephen L. Pentoney, Jr., Yorba Linda; David J. Rakestraw, Fremont, both of Calif.

[73] Assignee: Beckman Instruments, Inc., Fullerton, Calif.

[21] Appl. No.: 429,406

[22] Filed: Apr. 26, 1995

[51] Int. Cl.$^6$ ............................................. G01N 21/64
[52] U.S. Cl. ............................ 250/458.1; 250/459.1; 250/461.2
[58] Field of Search ...................... 250/461.2, 461.1, 250/459.1, 458.1

[56] References Cited

U.S. PATENT DOCUMENTS

| | | | |
|---|---|---|---|
| 5,091,652 | 2/1992 | Mathies et al. | 250/458.1 |
| 5,274,240 | 12/1993 | Mathies et al. | 250/458.1 |
| 5,371,016 | 12/1994 | Berndt | 435/291 |
| 5,418,371 | 5/1995 | Aslund et al. | 250/458.1 |

FOREIGN PATENT DOCUMENTS

| | | | |
|---|---|---|---|
| 64-88339 | 4/1989 | Japan | 250/458.1 |
| WO93/19205 | 9/1993 | WIPO . | |

OTHER PUBLICATIONS

J. F. Black, C. J. Summers, and B. Sherman, "Scanned-Laser Microscope for Photoluminescence Studies," *Applied Optics*, vol. 11, No. 7 (Jul. 1972) pp. 1553–1562.

"Capillary Array Electrophoresis Using Laser–Excited Confocal Fluorescence Detection", X.C. Huang, M.A. Quesada, R.A. Mathies, *Analytical Chemistry*, vol. 64, No. 8, (Apr. 15, 1992) pp. 967–972.

*Primary Examiner*—Constantine Hannaher
*Attorney, Agent, or Firm*—William H. May; Janis C. Henry

[57] ABSTRACT

A detection system for sequentially and repetitively scanning a plurality of sample volumes and detecting electromagnetic radiation emitting from each of the sample volumes includes a plurality of coplanar side-by-side capillaries each containing a sample volume, an electromagnetic radiation source, a mirror aligned to receive and reflect electromagnetic radiation, a scanner for moving the mirror, and a detector aligned to receive electromagnetic radiation collected from the sample volumes. In operation, the scanner adjusts the mirror position so that the mirror is positioned to receive the electromagnetic radiation from the electromagnetic radiation source and reflect the electromagnetic radiation sequentially and repetitively to the sample volumes. Emitted electromagnetic radiation from the sample volume is collected and directed to a detector where a signal is generated in response to the interaction of the electromagnetic radiation with the sample.

25 Claims, 9 Drawing Sheets

MULTICAPILLARY FLUORESCENT DETECTION SYSTEM

BACKGROUND OF THE INVENTION

1. Field of the Invention

The present invention relates to capaillary electrophoresis detection systems and methods detecting for separated analytes. In particular the present invention relates to high throughput, multiple capillary fluorescence detection systems capable of rapidly and sequentially detecting fluorescence with high sensitivity.

2. Description of Related Art

Capillary electrophoresis has found widespread application in analytical and biomedical research and has been employed for the rapid separation and analysis of charged species including synthetic polynucleotides, DNA sequencing fragments, DNA restriction fragments, amino acids, optical isomers of dansyl amino acids, and the separation of proteins, viruses and bacteria. Micellar electrokinetic capillary chromatography, isoelectric focusing, and on-column derivatization can all be performed on CE columns.

The advantages of CE arise from the use of a small inside diameter (20–200 μm) capillary. Very high electric fields can be applied along small diameter fused-silica capillaries. Since the electrophoretic velocity of the charged species is proportional to the applied field, CE can achieve rapid, high-resolution separation. Considerable heat is generated by Joule heating. However, the large surface-to-volume ratio of the capillary channel and the use of thin capillary walls (50–150 μm), allows rapid heat dissipation when used in connection with cooling systems.

Automated DNA sequencing has gained widespread attention in recent years. Current methods for sequencing strands of DNA typically apply Sanger-Coulson type chemistries and electrophoretic methods to separate the generated DNA fragments generated during the sequencing reaction. Because capillary electrophoresis and particularly CE combined with laser induced fluorescence (CE-LIF) detection offers rapid charged species analyte separations and high detection sensitivity, it is particularly attractive as a separation technique in DNA sequencing applications. In order to take advantage of laser induced fluorescence some current DNA sequencing reactions involve fluorescently labelling DNA fragments and then separating and detecting the sequencing reaction products using CE-LIF techniques.

Even though CE separations are rapid, the throughput associated with CE based DNA sequencing is generally less than that of conventional slab gels when only one capillary forms the separation system. In order to overcome this limitation it has been suggested that multiple capillaries be used in parallel to achieve the desired throughput. Of course, the increased throughput of a multiple capillary CE system becomes a costly and cumbersome system when used in combination with a multiplicity of discrete source and detector elements. Moreover, the discrete source/detector element approach also becomes much more complicated when the requirement for multiple wavelength monitoring is added.

A multiple capillary CE-LIF system which utilizes a confocal fluorescence scanner is described in U.S. Pat. Nos. 5,091,652 and 5,274,240. These scanners rely on moving continuously each capillary in an array of capillaries across the light path of a laser. Alternatively, it has been suggested that the whole optical head be moved across the array of capillaries in a "sweep" scan (HPCE Meeting, San Diego, 1994). Both of these approaches require the movement of relatively heavy system components as one capillary is moved from the light source and the next capillary is moved into the light source. Necessarily, a large amount of time is consumed in moving the system components. It is very likely that valuable separation information may be missed as a result of the lag time inherent in these systems. Moreover, the detection sensitivity attributed to fluorescence systems are somewhat compromised since the light source does not reside on an optimal part of the sample volume contained in each capillary, but is continuously scanned across the capillary.

Furthermore, since relatively heavy components are being moved in the prior art multicapillary detection systems, it is likely the momentum of the moving machinery will result in a gradual misalignment of the capillaries with respect to the light source or with the detector. Like the time delay problem, misalignments may lead to the loss of information and/or decreased sensitivity and increased detection limits. Also the motors and mechanisms required to move the capillaries necessarily result in additional cost associated with producing the scanner.

Accordingly, it is desirable to provide an economical highly sensitive, stable and rugged detection system for use in connection with high throughput separation systems. It is further desirable to provide an automated detection system for use in connection with multi capillary CE-LIF systems. Such a system should have the capability of providing multiple excitation wavelengths and detecting multiple emission wavelengths using a single detector.

SUMMARY OF THE INVENTION

The present invention is based upon the discovery that electromagnetic radiation from a single source can be directed to sample volumes in each of a plurality of closely spaced capillaries in a manner which allows sequential and repetitive detection of sample within the sample volumes by a single detector. Unlike prior art multiple sample detection systems which require continuously moving sample volumes to the electromagnetic radiation source, the present invention involves sequentially reflecting electromagnetic radiation from a mirror to a sample volume associated with each capillary in a step fashion. Advantageously, the detection system of the present invention eliminates the need to move bulky system components and allows the electromagnetic radiation source to remain on a selected sample volume for a preset time period. The result is improved detection sensitivity and a more economical and physically stable detection system.

Thus, the present invention provides a system for sequentially and repetitively scanning a plurality of sample volumes and detecting electromagnetic radiation emitting from each of the sample volumes. The system includes a plurality of coplanar side-by-side sample channels each containing a sample volume, an electromagnetic radiation source, a mirror aligned to receive and reflect electromagnetic radiation, a means for moving the mirror, and a detector aligned to receive electromagnetic radiation collected from the sample volumes. In operation, the means for moving the mirror adjusts the mirror position so that the mirror is positioned to receive the electromagnetic radiation from the electromagnetic radiation source and reflect the electromagnetic radiation sequentially and repetitively to the sample volumes. Emitted electromagnetic radiation from the sample volume is collected and directed to a detector where a signal is generated in response to the interaction of the electromagnetic radiation with the sample.

In preferred embodiments, the sample channels are capillary electrophoresis columns aligned in a coplanar side-by-side configuration to form a capillary array. The sample volume in each capillary column contains fluorescent labelled samples separated on an electrophoretic medium. In order to excite the samples, the mirror is aligned to receive an excitation radiation beam of a specific wavelength from the source and reflect the excitation radiation beam to the center of a given capillary. This excitation radiation beam excites fluorescent labelled sample causing a fluorescence emission which is collected and directed to a detector where a signal is generated in response to the interaction of the excitation radiation with the sample. This operation is performed sequentially and repeatedly with each capillary column in the array. The present invention has particular application in capillary electrophoresis systems used in combination with laser induced fluorescence detection in which high throughput is desired through the use of multiple capillaries. While those skilled in the art will recognize that there exists a multitude of applications, the present invention is described in the context of the analysis of fluorescent labelled DNA fragments obtained in DNA sequencing reactions.

Additional features, aspects and advantages of the invention will be more fully understood when considered in connection with the accompanying drawings and the detailed description which follows.

DETAILED DESCRIPTION OF THE INVENTION

The present invention is directed to detection systems for use in high throughput electrophoretic separation devices containing multiple separation channels. Because laser induced fluorescence detection is typically the method of choice for achieving high sensitivity detection following capillary electrophoresis separation, the present discussion is limited to CE-LIF embodiments. Those skilled in the art will recognize that alternate multicapillary detection systems including uv and visible detection are equally applicable.

Uniquely, the detection system of the present invention involves moving reflected excitation radiation sequentially and repetitively to sample volume contained in each capillary in a multicapillary array. Emitted fluorescence is collected and delivered to a detector which generates a signal whose magnitude is dependent on the amount of fluorescence. Because the excitation radiation is directed to each capillary without moving the capillary or moving the radiation source, no bulky system components are moved. This feature provides improved system reliability and detection sensitivity.

Figures 1, 1A:
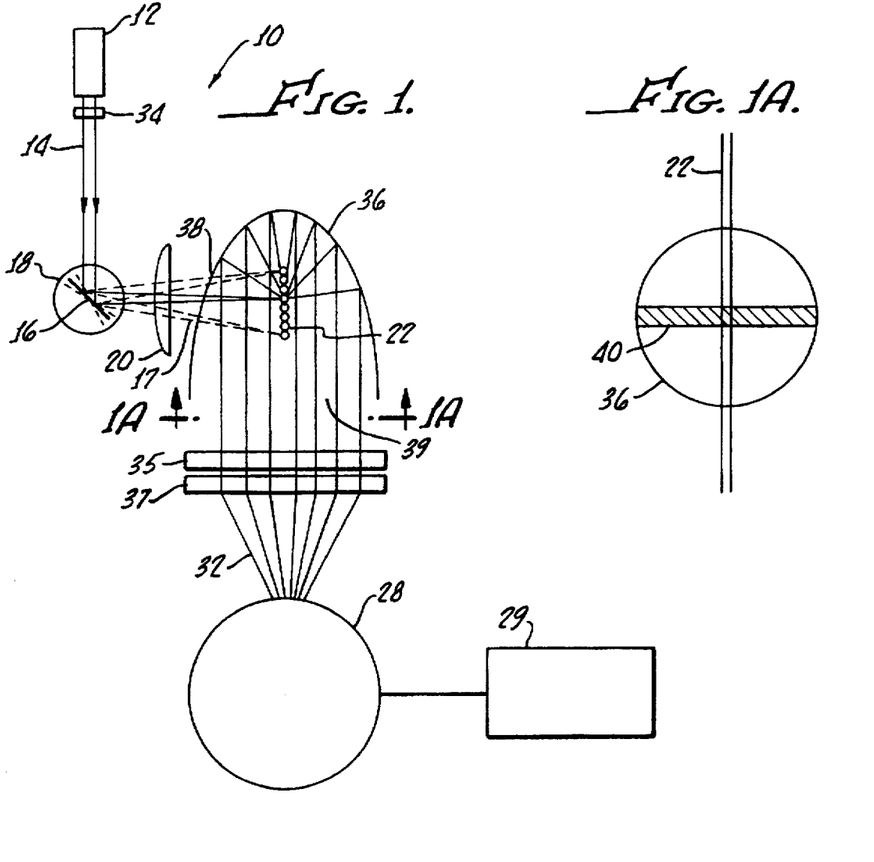
FIG. 1 is a schematic diagram of multicapillary a detection system of the present invention. The illustrated system is associated with a single laser excitation radiation source and a means for detecting a single fluorescence emission.
Figure 2:
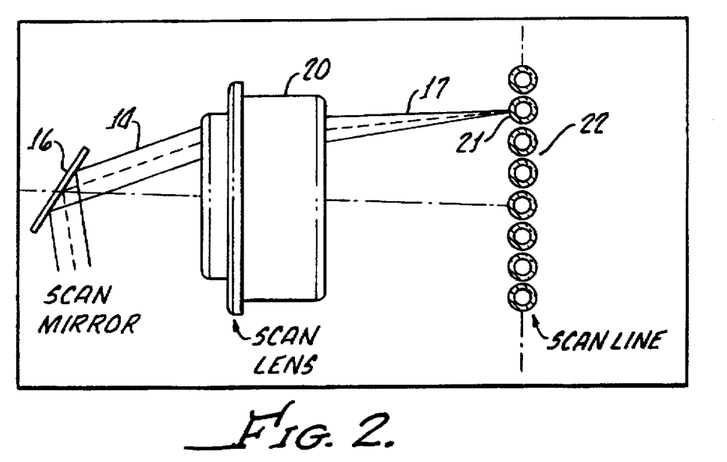
FIG. 2 illustrates the scan mirror, lens, and the orientation of the capillary array.
Figure 3:
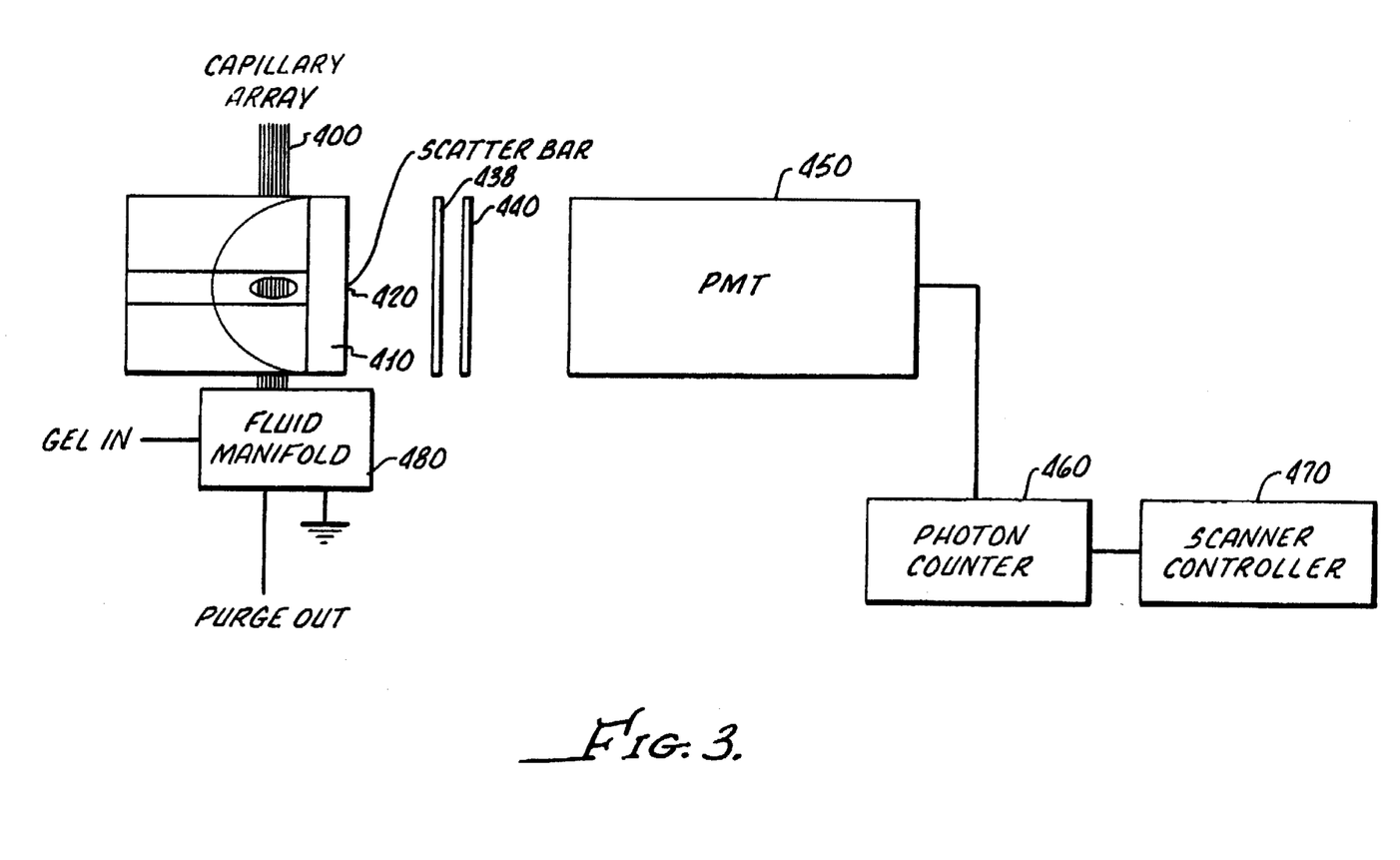
FIG. 3 is a schematic diagram of the parabolic mirror and array also showing the fluid manifold for controlling fluids into the capillaries.

FIG. 1 in combination with FIG. 2 and FIG. 3 illustrate one embodiment of the present invention in which a single laser is used to excite separated sample contained in a sample volume within each capillary of a capillary array. In this embodiment a single radiation source is utilized to provide radiation of predominately one wavelength and a single fluorescent label capable of excitation at the one wavelength is incorporated in the sample. Referring to FIG. 1 detection system 10 includes a laser radiation source 12, mirror 16 mounted on scanning means 18, focusing lens 20, an array 22 of eight coplanar capillaries, and a detector 28. Laser source 12 directs excitation radiation beam 14 to mirror 16 which is positioned by scanning means 18 so that excitation radiation beam 14 is reflected from mirror 16 to focusing lens 20. In FIG. 2, focusing lens 20 is shown in greater detail bringing the reflected excitation beam 17 in focus within a sample volume 21 at the center of a selected capillary within the array. The reflected excitation radiation beam 17 shown in FIG. 1 interacts with fluorescent labelled sample within the sample volume causing the sample to release emitted fluorescent radiation 32 which is directed to detector 28. Detector 28 provides a signal in response to the presence of the emitted radiation 32. A computing system, shown at 29 receives the signal for processing.

Following the release of emitted radiation 32, the scanner 18 causes mirror 16 to direct radiation beam 14 so that it is focused on the sample volume at the center of a different capillary in the capillary array. In such a manner scanner 18 and attached mirror 16 are used in combination with focusing lens 20 to sequentially bring the excitation beam 14 to a focus within the sample volumes of each capillary in the array.

From the foregoing description it can be seen that the detection system of the present invention incorporates an operating principle which involves step scanning a focused excitation laser beam in one direction across a capillary array and then quickly repositioning the mirror so that it is aligned to focus the excitation beam to the first capillary center. As used herein "step scanned" means that the excitation light source dwells on a capillary in the array for a preset time period then rapidly moves to the next capillary in the array where it again dwells for a preset period of time. The preset time period includes a measurement period or the time the excitation light is focused on a capillary in the array and during which time data is collected. Data collection occurs during each preset time period for each capillary sample volume.

The speed of the galvo-scanner allows maximization of measurement periods while minimizing transition periods. Those skilled in the art will recognize that this approach allows all capillaries of a multi capillary array to be addressed using only a single laser source and a single detector. Because a step scan mode is utilized and sample volumes receive focused excitation radiation, maximum laser intensity is delivered to the capillary centers during each measurement period.

Detection system 10 preferentially additionally includes filter 34 located between laser radiation source 12 and mirror 16. Filter 34 acts to remove any radiation provided by laser diode radiation source 12 having wavelengths outside of those necessary for excitation fluorescent labelled sample. Filter 34 additionally helps eliminate background scatter caused by radiation of undesired wavelengths. In order to collect and collimate emission radiation beam 32 and direct emission radiation beam 32 to detector 28, the present detector system preferably includes a high collection efficiency parabolic reflector 36. Each capillary of array 22 is positioned about the focal point of the parabolic reflector 36. Reflected excitation radiation beam 17 is directed from focusing lens 12 through aperture 38 located in parabolic reflector 36. Fluorescent emission radiation 32 from each capillary is collected by parabolic reflector 36 and directed through exit aperture 39 in parabolic reflector 36. A black bar 40 (scatter bar) is placed in a plane orthogonal to the axis of the capillary array, in order to obstruct intense laser light scatter surrounding the capillaries in this plane. The fluorescent emissions are directed through a series of optical filters 35 and 37 and is monitored using a photomultiplier tube 28. The filters are selected to block any scatter or background excitation radiation from the laser source and to allow transmission of emission fluorescence from the excited samples in the capillaries.

FIG. 3 shows the parabolic reflector of FIG. 1 with more detail. Capillary array 400 is shown positioned within the parabolic reflector 410 and the orientation of scatter bar 420 is indicated. Filters 430 and 440 and detector 450 is shown in relationship to a photon counter 460 and scanner controller 470 discussed with greater detail below. Also discussed below are components of the capillary electrophoresis fluid management system including fluid manifold 480.

In accordance with the present invention, radiation source 12 can be any source of electromagnetic radiation having the desired emission wavelength or wavelength spectrum. Those skilled in the art recognize that different fluorescent labels require different excitation energies or excitation wavelengths in order to obtain the desired emission properties. For purposes of the present invention, radiation sources are preferentially a laser diode having a characteristic excitation wavelength suitable for exciting fluorescence in the sample. Scanner 18 can be any device capable of very small precise movement such as a galvo scanner. Such scanners are particularly suitable in the practice of the present invention because they are a limited rotation servo motor capable of very rapid and precise movement. Mirror 16 is a plano mirror capable of receiving and reflecting excitation radiation beam 14.

For purposes of illustration and as shown in FIG. 1 the present embodiment utilizes a capillary array 22 of eight coplanar capillaries positioned side-by-side. The array is positioned so that focused excitation beam 17 is perpendicular to the length of the capillaries. The capillaries are fabricated of silica and have dimensions which can vary with the particular application. Suitable capillary dimensions can be typical of those utilized in capillary electrophoresis methods and include lengths of between 20 cm and 500 cm and diameters of between 20 µm and 500 µm. Preferred capillaries have relatively large wall thicknesses of 50 µm. Each capillary is connected to a single high voltage power supply which provides the potential for the electrophoretic field. In order for the excitation beam to enter the sample volume and for the emission beam to leave the sample volume, each column contains a transparent "window" surrounding the sample volume which is typical of silica capillaries used in CE applications.

Detectors suitable in the practice of the present invention can be any of a variety of devices used to generate signals from electromagnetic radiation including, but not limited to, charge coupled devices, avalanche photodiodes, photodiodes and photomultiplier tubes. Preferred detectors are photomultiplier tubes operated in a photon counting mode. Alternatively, a form of DC averaging detection can be utilized in the present detection systems. DC averaging detection involves an amplifier bandwidth which is fast enough to allow proper signal assignments with gating periods but which still possessed a sufficiently long time constant to allow extraction of accurate DC light levels from experimental photocurrents would be feasible. This mode of detection does not offer the performance of photon counting but may offer a slight cost savings. DC averaging also provides superior performance at higher light levels for application less demanding than DNA sequencing.

Another embodiment of the present invention involves detecting multiple samples which are differentiated from each other by the wavelength of their fluorescence emission. This embodiment involves the use of more than one fluorescence label and the ability to excite and detect fluorescence emission of more than one wavelength. For purposes of illustration up to four different fluorescent dyes, each of which has a different excitation wavelength and emission wavelength are incorporated in the detection system. As may be expected the ability to excite multiple fluorescent labels may require more than one excitation radiation source in order to provide the required full range of excitation radiation wavelengths. Similarly, the ability to detect multiple emission radiation wavelengths may require precisely timed moving filters so that emission radiation of specific wavelength is available at the detector at specific timed intervals.

A multicapillary and multiwavelength detection system described herein provides a particularly suitable system for detecting DNA fragments obtained in DNA sequencing reactions where each of four nucleotide bases is identified by the emission wavelength of its unique fluorescent label. Four color DNA sequencing reactions and the subsequent separation of DNA fragments resulting from the reactions are known and will not be discussed in detail here.

Figure 4:
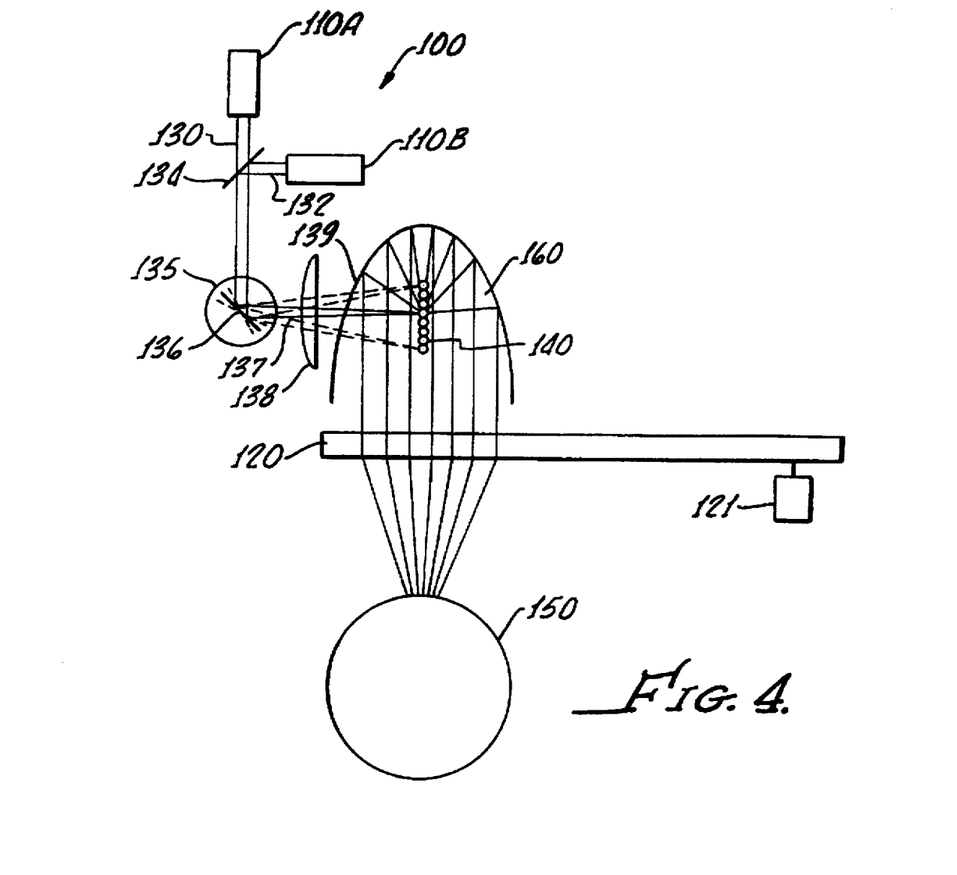
FIG. 4 is a schematic diagram of multicapillary detection system of the present invention. The illustrated system is associated with two laser excitation radiation sources and a means for detecting multiple fluorescence emissions.

A schematic diagram illustrating a detector system suitable for use in a four color DNA sequencing reaction is illustrated in FIG. 4. The detection system 100 of FIG. 4 contemplates the detection of four different fluorescence labels requiring two laser sources 110A and 110B in order to provide two excitation radiation beams 130, 132 of differing wavelengths. For purposes of illustration, laser source 110A is capable of exciting a sample fluorescence attributed to a first and second fluorescence dye. Similarly, laser source 110B is capable of exciting a sample fluorescence attributed to a third and fourth fluorescent dye.

Figure 5:
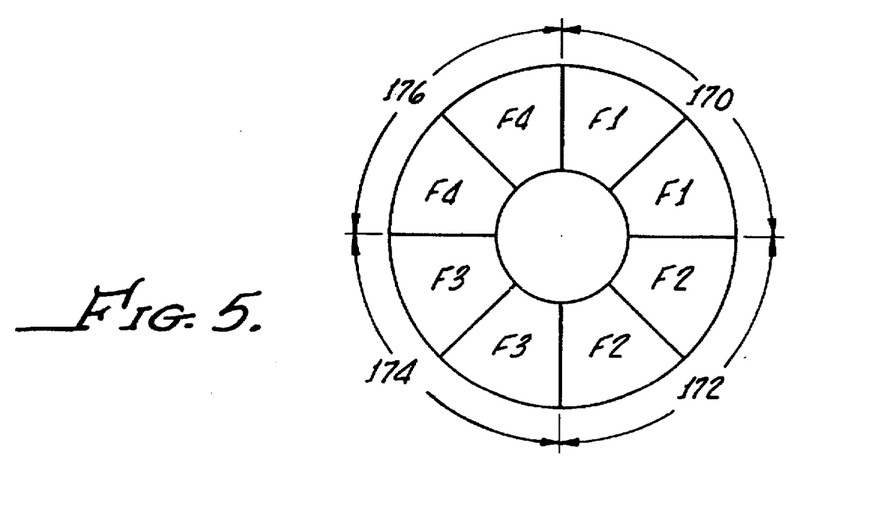
FIG. 5 is a detail of a filter wheel useful in the practice of the present invention.

During operation, laser excitation radiation source 110A is turned on and combiner mirror 134 directs the laser excitation beam 130 from source 110A onto mirror 136. Reflected excitation beam 137 passes through focusing lens 138 and aperture 139 of parabolic reflector 160 and onto a sample volume of first capillary within capillary array 140, as described above. Fluorescence emission radiation from the sample volume of the first capillary is collected and passed through a filter wheel 120. FIG. 5 provides a front facing view of filter wheel 120. Referring to FIG. 4 and FIG. 5, emission radiation is passed through first filter 170 which is selected to block light at the wavelength of laser source 110A and to transmit fluorescence emitted by the first fluorescent dye. Fluorescence transmitted by the first filter 170 is detected at detector 150 and transmitted to computing means 160 for processing. Motor 121 then rotates filter wheel 120 to bring a second filter 172 into the fluorescence emission beam. The second filter 172 is designed to block light at the wavelength of the laser source 110A but to transmit fluorescence emitted by a second fluorescence dye. Fluorescence transmitted by the second filter 172 is measured by detector 150.

After detector 150 detects fluorescence emissions attributed to the first and second fluorescence dyes in the first capillary in the array, laser source 110A is turned off and laser source 110B is turned on. The beam from the laser is directed onto the first capillary, as described above. Fluorescence from the excited capillary is collected and passed through a third filter 174 located in filter wheel 120 which is rotated into position in synchrony with the switching on of laser source 110B. The third filter 174 is designed to block excitation radiation at the wavelength of laser source 110B but to transmit fluorescence emission radiation of a third fluorescent dye. Fluorescence emission transmitted by the third filter is detected at detector 150 and the detection signal is transmitted to a computing means (not shown) for processing. Motor 121 then rotates filter wheel 120 to bring a fourth filter 176 into the fluorescence emission radiation beam. Fourth filter 176 is designed to block light at the wavelength of the laser source 110B but to transmit fluorescence emission by a fourth fluorescence dye. Fluorescence transmitted by the fourth filter is measured.

After measurements corresponding to each of the four dyes have been taken, laser source 110B is turned off, the galvo-scanner 135 moves mirror 136 so that it directs the reflected excitation radiation beam 137 onto a second capillary in the array and the first laser is turned on. The sequence described above is then repeated until measurement for each of the four dyes are taken in the second capillary. This sequence is repeated for each of the capillaries in the array. After measurement for each of the four dyes in each of the capillaries in the array are taken the galvo-scanner moves mirror 136 so that it is positioned to direct the reflected beam onto the first capillary in the array. The whole sequence is then repeated until data collection is completed.

Those skilled in the art will recognize that the foregoing description advantageously provides detection data for each of multiple fluorescence dyes in each of multiple capillaries contained in an array of capillaries. Each fluorescent signal is assigned to its respective capillary by synchronizing the galvo-scanner positioning with the photon counter gating periods. In this manner the location and identity of the fluorescent sample in each sample volume can be identified at any time period during the analytical procedure. The combination of galvo scanner, mirror and focusing lens allows rapid sample volume excitation and detection. In fact, the length of time required to make a capillary to capillary transition is on the order of 400 μsec. Rotating filter wheels provide a convenient means for filtering and transmitting radiation of desired wavelength at preset time intervals to the detector. Other filtering means including but not limited to tunable liquid crystal filters are suitable in the practice of the present invention. Such tunable liquid crystal filters are attractive filtering option because they can accommodate changes and/or additions to the transmission functions. It also eliminates a spinning component of the optical system.

Photomultiplier tubes and spinning filter wheels can be replaced by a grating in combination with either a photodiode array or a charge coupled detector (CCD).

It should also be noted that several alternative approaches for light delivery and fluorescence collection are also of use in the present invention. These alternate approaches include: the use of dedicated lasers and detectors for each capillary; the use of imaging optics, a dispersive element and a CCD (charged coupled device) array detector; the use of a fiber optic switching device for excitation; the use of a binary optic beam-splitter for excitation; the use of a tunable, liquid crystal emission filter; and the use of a spinning, faceted mirror for excitation.

As noted above, fluorescent dyes capable of being attached as labels to sample components so that they can be easily detected subsequent to their electrophoretic separation are advantageously used in the present invention. The choice of fluorescent dyes for any given application depends upon the sample components of interest, the detection system configuration, the availability of specific lasers and detectors. Typically fluorescent labels are selected for their excitation requirements and their emission characteristics. Moreover, one skilled in the art will realize that different lasers and filters or different combinations of lasers and filters may be required to accommodate the different properties of the fluorescent labels or combination of labels. Ideally, fluorescent labels utilized in a multiple fluorescent dye system of the present invention are capable of utilizing a common excitation radiation wavelength and provide emission radiation of wavelengths sufficiently different to allow their resolution. Fluorescent labels and labeling chemistry are well known in the art and will not be discussed further here. A wide variety of fluorescent dyes and fluorescent labels are commercially available and in many cases they can be purchased in an activated form. This provides a ready means for their attachment to samples prior to their electrophoretic separation.

Advantageously, the detection system of the present invention can be used to align the capillaries so that each capillary is in an optimum position with respect to the laser excitation beam and detector. Copending U.S. patent application Ser. No. 08/409,557, which is hereby incorporated herein by reference, describes such an alignment procedure. Once the capillaries used in the present invention are aligned in accordance with the method taught in the referenced patent application, they remain aligned for a substantial period of time. This is because the present invention does not rely upon bulky component movement in order to scan the capillaries. Such bulk movement causes frequent misalignment of component parts which results in loss of sensitivity and can lead to total loss of signal.

As already mentioned, a preferred application of the present invention is the analysis of fluorescent labelled DNA fragments resulting from Sanger Coulson DNA sequencing reaction chemistries. Those skilled in the art will appreciate that the extremely low detection limits are required in order to successfully apply CE based separations to DNA sequencing applications. The present invention provides these low detection limits and advantageously results in high sample throughput.

It is generally accepted that, when using CE/LIF based DNA sequencing, an optical system capable of exhibiting fluorescent label concentration detection limits in the 10 pM (picomolar) range will produce electropherograms with sufficient signal-to-noise ratios to allow sequence calling from standard scale sequencing reactions. In the Examples which follow, the ability of the present detection system to provide reliable DNA sequencing data is demonstrated.

EXAMPLE 1

Figure 6:
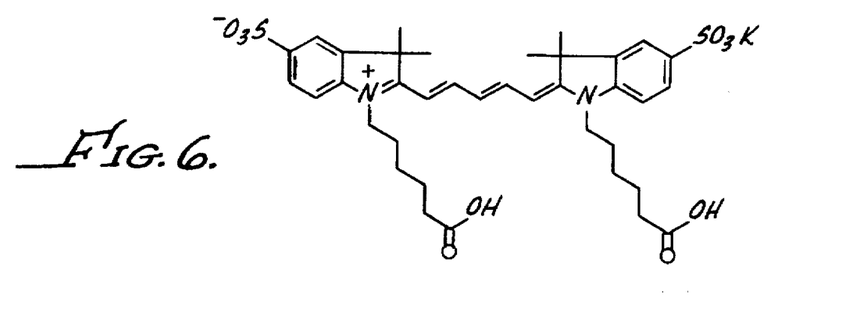
FIG. 6 illustrates the structure of fluorescent label $D_{673}$.

In this experiment the performance of a multicapillary detection system of the present invention is demonstrated in the analysis of fragments obtained from DNA Sanger-Coulson DNA sequencing reactions. The sequencing reactions involved utilized a primer oligonucleotide containing a fluorescent labeled known as $D_{673}$. The structure of $D_{673}$ is shown in FIG. 6. This fluorescent label can be excited with excitation radiation of around 639 nm and its emission radiation maximum occurs at 673 nm.

Figure 7:
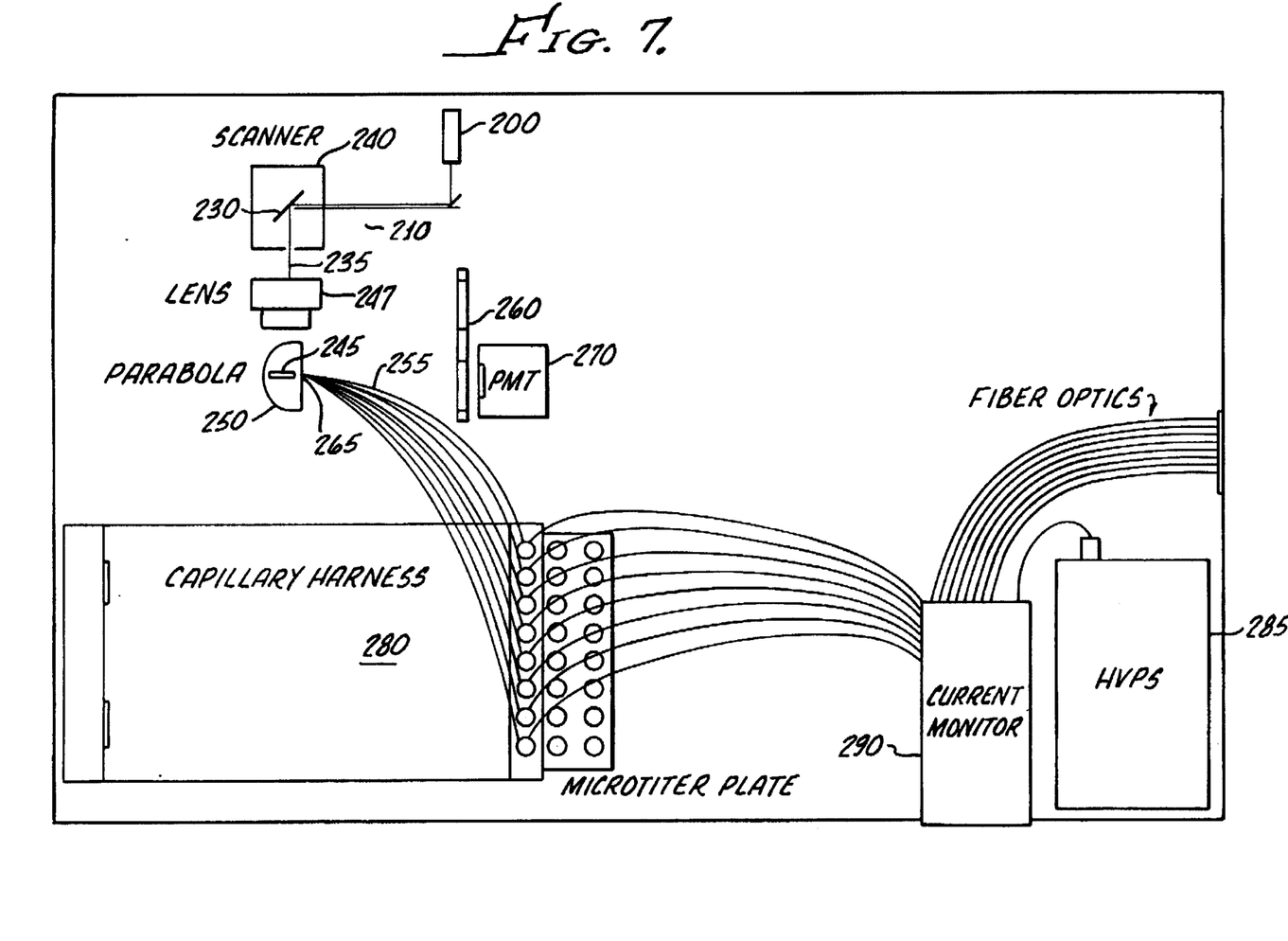
FIG. 7 shows a general system layout for using the detector system of the present invention.

The system used to perform the experiments is shown in general layout form in FIG. 7. The output of a red diode laser 200 (639 nm, 1.3 mW, Model TSX-1, purchased from Uniphase) was directed through a laser line filter 210 (640 nm, 7 nm FWHM (full width, half maximum) supplied by Barr Associates) and was reflected at 90° off a small mirror 230 (Model M0540V, supplied by General Scanning, Inc.) which was fastened to the limited rotation drive shaft of a galvanometer scanner 240 (Model G120DT supplied by General Scanning, Inc.). The beam 235 reflected off the scan mirror was directed through a planoconvex lens (Model 41340 supplied by Oriel, Inc.) and was focused through an aperture 245 in the side of a 1" diameter parabolic reflector 250 (Model 1587 supplied by Carley, Inc. of Torrance, Calif.). The beam was focused into the center of any one of eight fused silica capillaries (TSP100200 supplied by Polymicro Technologies, Inc. of Phoenix, Ariz.) which were held in a linear array 255 about the focal point of parabolic reflector 250. The focused beam passed through the capillary bore and exited the reflector through a second aperture 265.

Fluorescent emissions originating at the capillary bore were collected and collimated by the parabolic reflector 255. The emission was directed through a series of optical filters, shown collectively at 260, consisting of (1) a long pass filter with high rejection at the laser wavelength (650 nm long pass custom made by Barr Associates) and (2) a bandpass filter (680 nm, 10 nm FWHM by Oriel, Inc.). The filtered emissions were then focused onto a photocathode of an end-on photomultiplier tube 270 (Model #C31034, RCA, or Model 4632 supplied by Hamamatsu) using a biconvex lens (not shown).

The photomultiplier tube 270 was operated in the photon counting mode. Photocurrent pulses were voltage converted, amplified, subjected to discrimination using a Model SR445 Fast Preamplifier and Model SR 400 Discriminator (supplied by Stanford Research Systems, Inc.) and then sent to a counter (Model 3615 Hex Scaler supplied by Kinetic Systems). Photon counter gating and galvo control through a DAC output (Model 3112, 12-Bit DAC supplied by Kinetic Systems) were synchronized using a digital delay/pulse generator (Model DG535 supplied by Stanford Research Systems, Inc.). Communication with a PC computer 29 was accomplished using a parallel register (Model PR-604 supplied by DSP Technologies, Inc.), a CAMAC controller card (Model 6002, supplied by DSP Technologies, Inc.) and a PC adapter card (Model PC-004 supplied by DSP Technologies, Inc.).

Eight capillary array 255 was connected to a high pressure fluid manifold (not shown in FIG. 7) located beneath parabolic reflector 250. The positioning of the high pressure fluid manifold is illustrated in FIG. 3 where it is shown at 480. This fluid manifold causes polyacrylamide separation gel to pass from a gel syringe pump into the capillaries, in gel replacement mode, or to pass through the capillary ends and out to waste, a gel purging mode. The fluid manifold 13 also served as the "outlet buffer reservoir" in the sense that high voltage circuit grounding was made through a metal fitting in the manifold block. The inlet end of the capillary array was connected to a capillary harness 280 positioned above a microtiter plate.

The output of a single high voltage power supply 285 was split into eight separate paths inside of current monitoring compartment 290. Data acquisition was made by directly measuring the frequency or by carrying out a frequency-to-voltage conversion and then measuring the voltage.

The detector system was operated by initiating a capillary array scan every 0.5 seconds for an array scan rate of 2 Hz. A pulse generator, not shown, delivered a 16 Hz pulse train with each pulse triggering the galvoscanner to cause mirror 230 to redirect excitation radiation to a new capillary. The pulse generator set a brief delay following each new mirror position and then gated the photon counting interval for each capillary dwell time. Table I lists the relevant timing parameters for this experiment.

TABLE I

| One Color Timing Parameters | |
| --- | --- |
| Array Scan Rate | 2.0 Hz |
| Single Scan Period (8 capillaries) | 0.5 s |
| Total Dwell Per Capillary | 62.5 ms |
| Typical Over-estimated Dead Time | 5.0 ms |
| Typical One Color Count Interval | 57.5 ms |

The near IR extended photomultiplier tube 270 was used in a photon counting mode of operation for three reasons. This mode is desirable because photon counting provides the best performance for the light levels used in an analysis system where there are on the order of 100 to 400 photon counts per msec. Also, photon counting is a very fast mode of detection, making it readily compatible with the scanning approach in which detector signals must be rapidly assignable to the appropriate capillary and spectral channels. Third, photon counting is a very convenient mode of detection to synchronize with the galvo-step-scanning.

Figure 8:
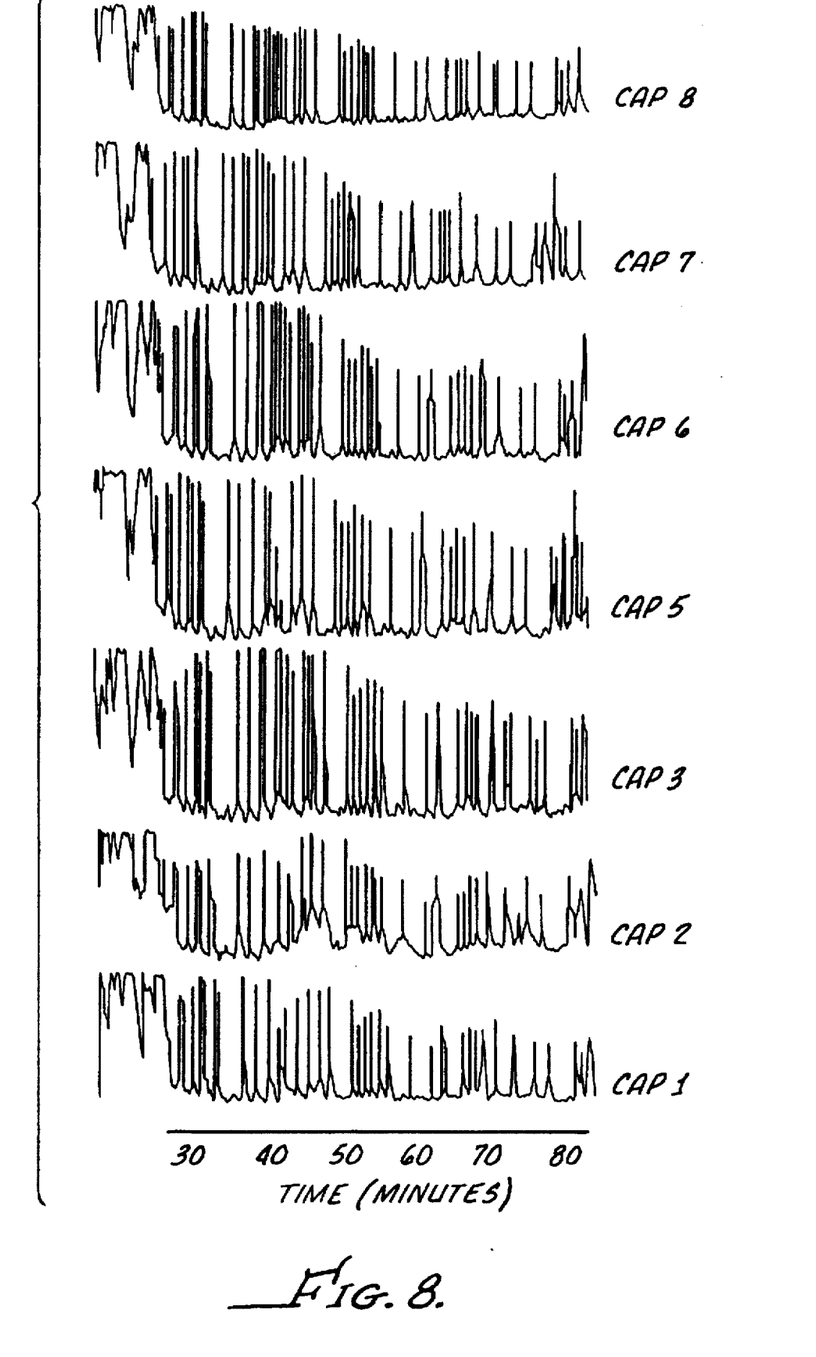
FIG. 8 is a set of electropherograms obtained utilizing the detection system of the present invention to analyze DNA fragments obtained from a DNA sequencing reaction.

The $D_{673}$ labeled DNA fragments obtained from the sequencing reactions were separated by loading the reaction samples onto the just described system. FIG. 8 shows eight electropherograms measured using the galvo-scanner system. (Capillary 4 was not displayed in this plot because the current failed early in the run.) The data shown in these electropherograms is scale expanded showing the results of separating DNA sequencing fragments generated over the size range 35 to 323 bases. The detection system of the present invention provided excellent signal-to-noise ratios. These results demonstrate that the scanning parameters used in this experiment combined with a galvoscanner based method for moving the excitation radiation beam in step fashion to sample volumes in each capillary provides high sensitivity detection of DNA sequencing fragments.

During the course of this experiment the galvo-scanner approach was demonstrated to be very versatile over the range 1 to eight capillaries in the configuration described here. For example, the galvo-scanner need not scan all eight capillaries or any number of capillaries in any particular order. It was also a simple matter to alter the timing sequence in order to address any number of capillaries over this range while maintaining an optimum duty cycle. Accommodating both four and eight capillary arrays is a simple matter using this approach.

The galvoscanner's ability to precisely control mirror movement and direct the excitation beam to the capillary sample volume was exceptional. The time required to perform a capillary-capillary transition (a 200 μm distance) was 400 μsec, the return scan to repeat cycle was 1 msec (capillary 8 to capillary 1 or about 1400 μm. The time fraction of the scan which was spent actually moving the galvoscanner and mirror was 0.79% while the time fraction actually spent dwelling at the sample volume and taking data was 99.24%.

EXAMPLE 2

Figure 9:
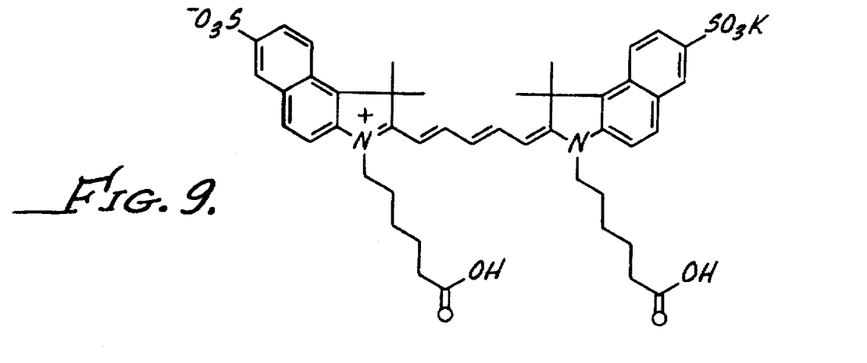
FIG. 9 illustrates the structure of fluorescent label $D_{715}$.
Figure 10:
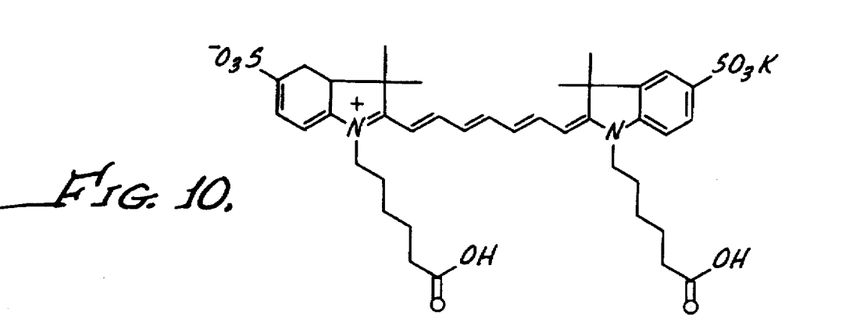
FIG. 10 illustrates the structure of fluorescent label $D_{775}$.
Figure 11:
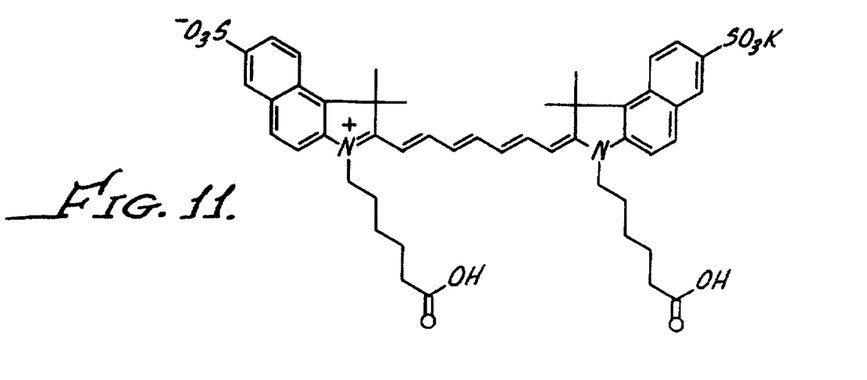
FIG. 11 illustrates the structure of fluorescent label $D_{820}$.

The following example demonstrates the detection of four fluorescent labels utilizing the detection system of the present invention. Significantly, in this experiment, the gating interval for photon counting detection was decreased by at least a factor of 4 resulting in a substantial decrease in measurement time and potentially a decrease in performance. The four fluorescent labels include $D_{673}$ described above and shown in FIG. 6; $D_{715}$ shown in FIG. 9, capable of excitation with a 650 nm laser line and having an emission radiation of 715 nm; $D_{775}$ shown in FIG. 10, capable of excitation with a 750 nm laser and having an emission radiation of 775 nm; and $D_{820}$ having the structure shown in FIG. 11, capable of excitation with a 750 nm laser and having an emission radiation of 820 nm. Those skilled in the art will recognize that the combination of these four fluorescent labels allow the detection of separated DNA fragments from sequencing reactions to be excited and detected using a 2 laser source system and a single detector. That is, by selecting two laser sources which provide the range of about 650 to 750 excitation radiation and providing a detector capable of detecting fluorescence emission from 673 nm to 820 nm, the detection system of the present invention will effectively excite and detect the separated DNA fragments.

Preliminarily, since exciting and detecting multiple fluorescent labels requires decrease in measurement time for each capillary dwell, the effect of decreased measurement time upon the signal-to-noise ratio was investigated using the single fluorescent label described in Example 1. This was performed by simply decreasing the gating period associated with the single fluorescent label experiments in order to mimic that of the four fluorescent label experiment (approximately 10 msec). The tests showed that the decreased measurement time provided sufficient signal to the detector.

The four fluorescent label test system was performed on a system similar to that shown in FIG. 7, except that two diode lasers were used as excitation radiation sources with an optics layout as shown in FIG. 4. Additionally, the filter shown collectively at 260 in FIG. 7 were replaced with a filter wheel as shown in FIG. 5. The two diode lasers were a 650 nm, 1.3 mW laser supplied by Uniphase and 750 nm, 1.3 mW, also supplied by Uniphase.

As described above in Example 1, fluorescent emissions originating at the capillary bore were collected and collimated by the parabolic reflector. The emission was directed through an optical filter which was included in a filter wheel. The filter wheel included four quadrants. In each of the quadrants were different filters as follows:

The filter in quadrant one had a high rejection at the 650 nm laser wavelength and high transmittance in the range of the fluorescence emitted by $D_{673}$;

The filter in quadrant two had a high rejection at the 650 nm laser wavelength and high transmittance in the range of the fluorescence emitted by $D_{715}$;

The filter in quadrant three had a high rejection at the 750 nm laser wavelength and high transmittance in the range of the fluorescence emitted by $D_{775}$; and The filter in quadrant four had a high rejection at the 750 nm laser wavelength and high transmittance in the range of the fluorescence emitted by $D_{820}$.

Figure 14:
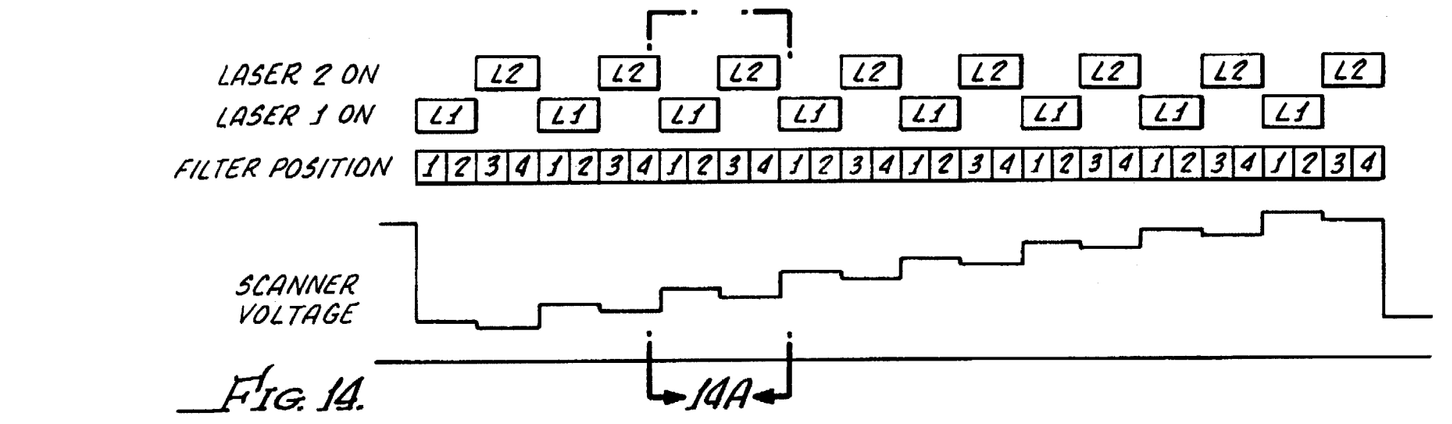
FIG. 14 illustrates the timing scheme for an eight capillary, four color experiment with a scan rate of 2 Hz.
Figure 14A:
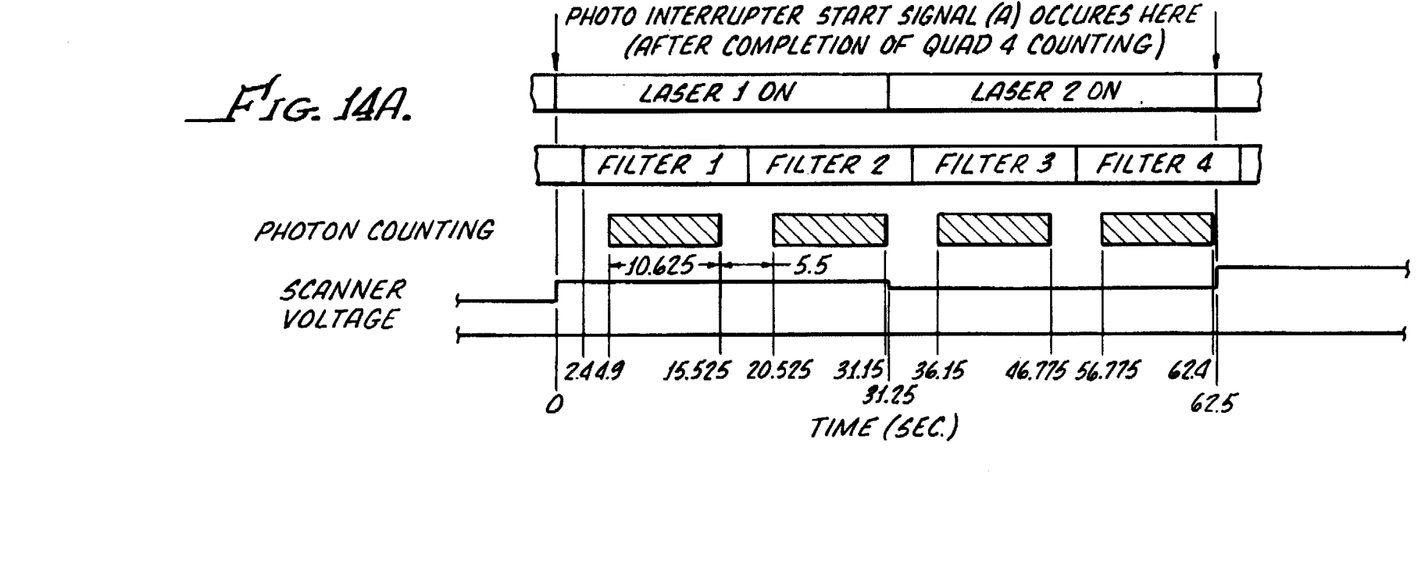

In operation the 650 nm laser was turned on to illuminate a capillary and the filter wheel was rotated to bring quadrant one into the laser beam. The filtered emissions were then focused onto a photocathode of the end-on photomultiplier tube using a biconvex lens and a reading corresponding to $D_{673}$ was taken. The filter wheel was then rotated to bring quadrant two into the laser beam and a reading corresponding to $D_{715}$ was taken. The 650 nm laser was then switched off and the 750 nm laser was switched on. The filter wheel was then rotated to bring quadrant three into the laser beam and a reading corresponding to $D_{775}$ was taken. The filter wheel was then rotated to bring quadrant four into the laser beam and a reading corresponding to $D_{820}$ was taken. A timing diagram for operation of the galvo-scanner is shown in FIG. 14.

The photomultiplier tube was operated in the photon counting mode as described above in Example 1 and in all other respects the capillary system and fluid manifold operation were as described above.

Figure 12:
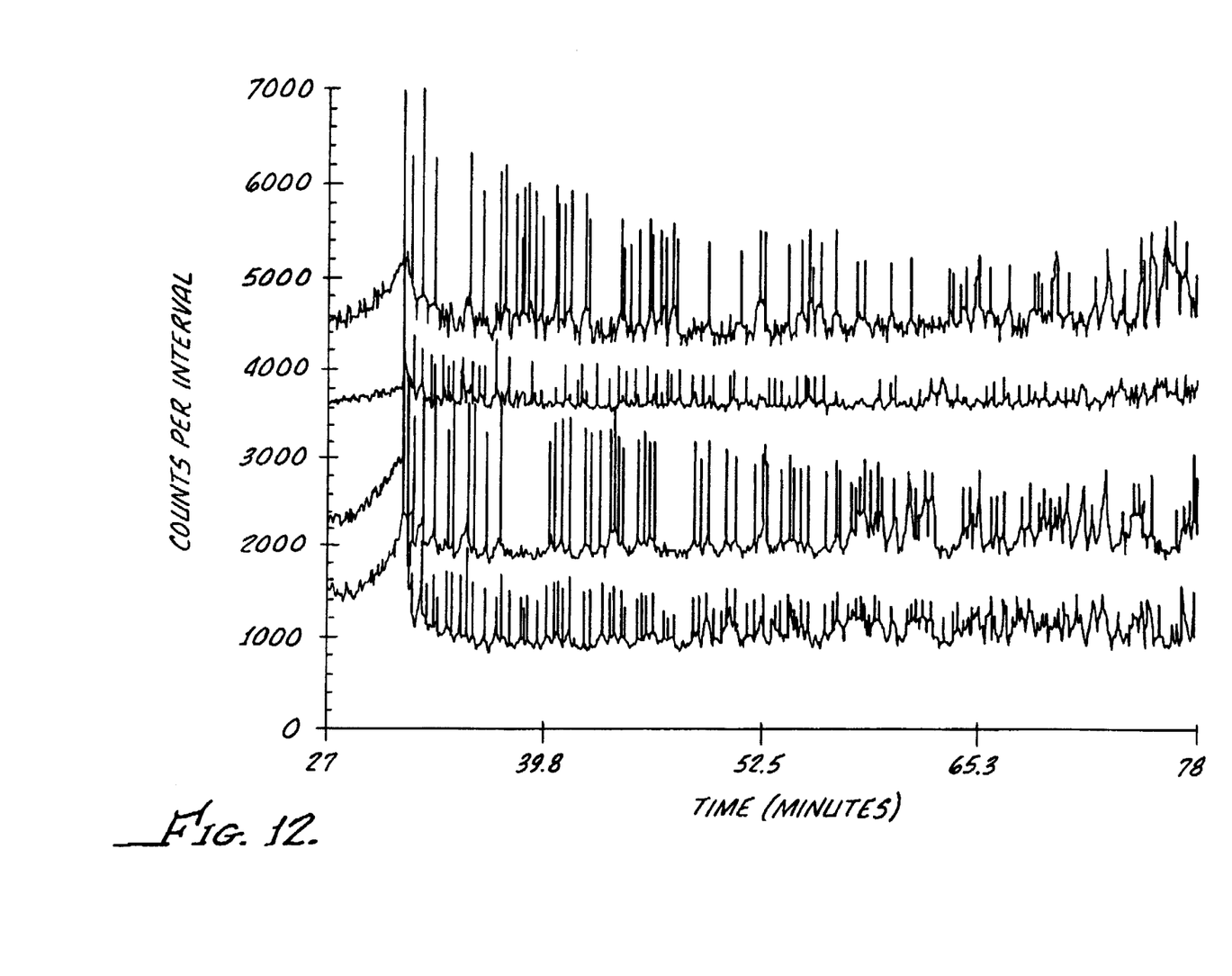
FIG. 12 is four electropherograms obtained using the detector system of the present invention. The electropherograms are those of separated DNA fragments obtained in a DNA sequencing reaction using labeled primer.

DNA fragments were generated in a Sanger-Coulson type sequencing reaction by labelling oligonucleotide primer with each of the four fluorescent labels described above. The DNA template sequenced was mM13mp18. The fragments separated were on the foregoing described system. FIG. 12 illustrates electropherograms obtained from each of the four channels from a single capillary. The data demonstrates that the detection system of the present invention is capable of causing the excitation of multiple fluorescent labels and detecting emission of the same multiple florescent labels simultaneous with their effective electrophoretic separation.

EXAMPLE 3

In order to evaluate the performance of the detector system of the present invention on the discrimination of multiple fluorescent labelled analytes, a "signature" of each of the four fluorescent labels ($D_{674}$, $D_{715}$, $D_{775}$, and $D_{820}$ was obtained. The signature indicates the degree to which the filter wheel in the present system eliminates fluorescent emission attributed to the remaining three fluorescent labels. The experiments involved analyzing a solution of 2.6 nM $D_{673}$, 4.3 nM of $D_{715}$, 6.9 nM of $D_{775}$, and 2.9 nM of $D_{820}$.

Figure 13:
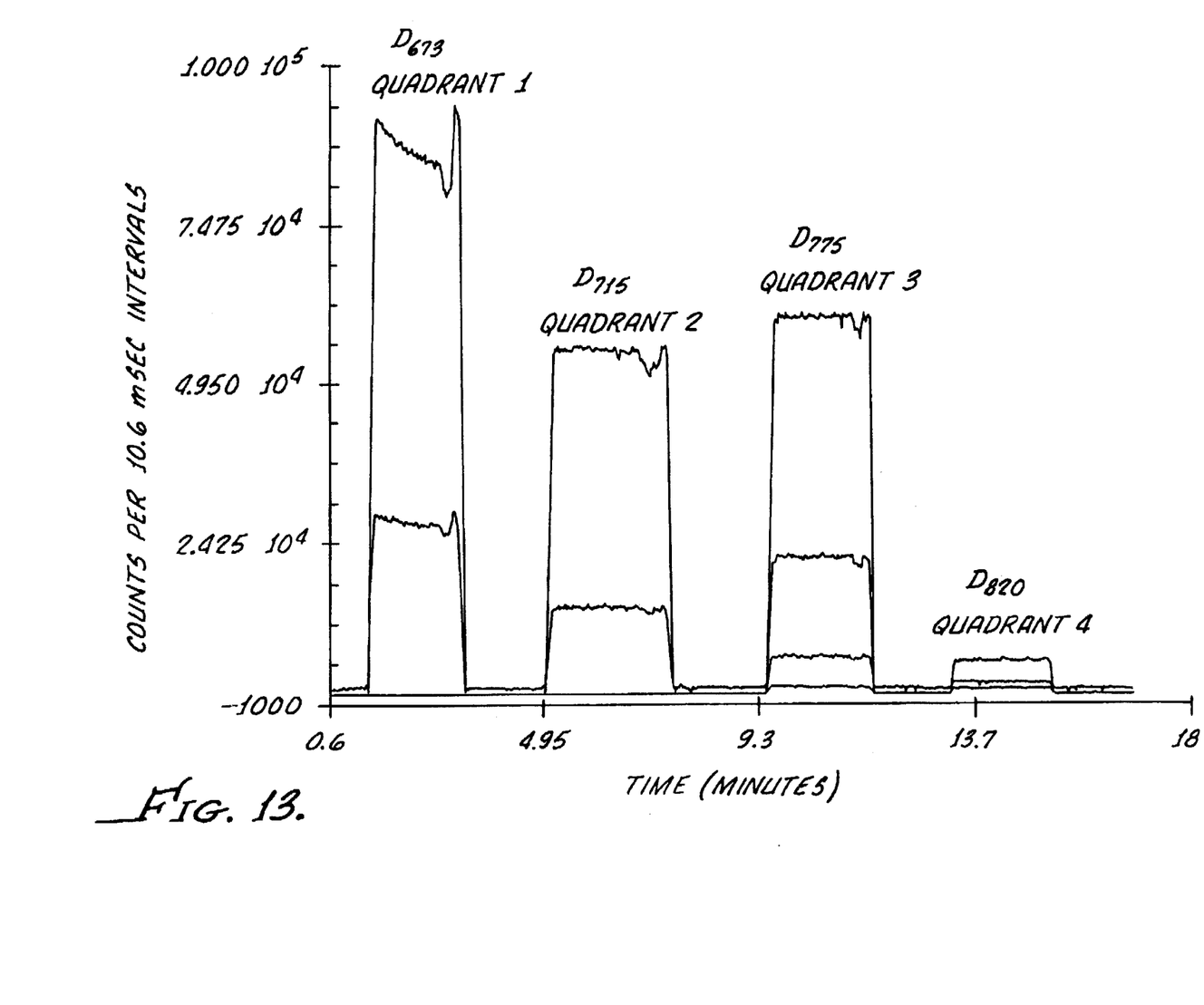
FIG. 13 is a fluorescent signature obtained for each of 4 different fluorescent labels while obtaining parallel sets of data for emissions from each fluorescent label.

Thus, referring to FIG. 13, when data is being collected during the measurement time with the filter wheel in quadrant 1 $D_{673}$ is being measured. FIG. 13 indicates that data collected in quadrant 1 is predominately $D_{673}$ signal. Similarly, in quadrant 2 the data is predominately $D_{715}$ signal which is supported by the data. From the high counts per 10.6 msec, this experiment demonstrates the effective discrimination of these fluorescent labels and also demonstrates picomolar detection limits for $D_{673}$, $D_{715}$, $D_{775}$. Clearly, the high sensitivity detection accompanying their use in the detection system of the present invention indicates that these fluorescent labels are suitable for use in multicapillary CE-LIF based separations.

A common labelling approach in DNA sequencing reactions involves labelling dideoxy terminators with a fluorescent label. DNA fragments resulting from sequencing reactions are then labelled at their termination. The above data obtained for the four fluorescent labels indicates that labeled dideoxy terminators such as ($D_{673}$-ddATP, $D_{715}$-ddUTP and $D_{775}$-ddGTP) can be observed with picomolar detection limits for $D_{673}$-ddATP and $D_{715}$-ddUTP and 20 pM detection limits for $D_{775}$-ddGTP can be achieved. Advantageously, it is known that these fluorescent labels can be incorporated in dideoxy terminators which incorporate in Sanger-Coulson sequencing reactions. Thus, the high sensitivity detection accompanying their use in the detection system of the present invention indicates that these fluorescent labels are suitable for use in multicapillary CE-LIF based separations of DNA fragments using the detection system of the present invention.

The present invention is not to be limited to the specific embodiments which are shown or described above and which are merely illustrative. Various and numerous other arrangements may be devised by one skilled in the art without departing from the spirit and scope of this invention. For example, the detection system of the present invention may be applicable to detection based upon phosphorescent labels, chemiluminescent labels, or electrochemiluminescent labels.

The detection system of the present invention has utility in numerous applications in addition to the separation and detection of DNA fragments resulting from DNA sequencing reactions. In the discussion which follows, a number of applications are described, all of which are benefitted by the high throughput and detection sensitivity characteristic of the present invention.

One application for a high-throughput CE-LIF system equipped with a detection systems described herein involves the analysis of DNA amplification products (for example, PCR products). Simple assays for the presence of amplified DNA are unacceptable because of the possibility of nonspecific DNA amplification.

One current method for analyzing for the presence of amplified DNA involves the use of hybridization probes. In spite of its many advantages hybridization the laborious washing steps take time and automating such liquid handling requires sophisticated equipment. In addition, the cost of the probes and the format in which they are presented make this approach expensive. Direct DNA size analysis by automated CE-LIF using the high throughput detection system of the present invention is faster and less expensive than hybridization-based assays. Utilizing the detection system of the present for such applications allows the sample and standard to be run together in the parallel, using different fluorescent labels to distinguish them.

Another useful attractive application of the high throughput multicapillary detection system of the present invention involves HLA typing. HLA typing is required for organ and bone marrow transplantation and optimal discrimination among the currently characterized loci by sequence-specific primers (SSP) requires as many as 60 PCR reactions per donor. Thus, automating the separation, size determination and genotype assignment is highly desirable. It should also be noted that HLA polymorphisms also provide useful markers for paternity determinations and individual identification in forensic medicine.

Another application related to HLA typing is genotyping via polymorphism mapping, common in hybrid plant analysis. In this application, short regions of the genome which are highly polymorphic (frequently variable in length among different individuals) and associated with regions of interest in the genome (for example, a desirable trait) are identified and primers which hybridize to highly conserved sequences (sequences which are the same in all individuals) which flank the variable regions are used to amplify the variable region. The size information obtained from a set of polymorphic sites provides information about the parental origin of different genes within a hybrid and allows selection of individuals for further analysis. The set of polymorphic sites can be analyzed in parallel, requiring high throughput, or simultaneously (multiplexed) if different fluorescent labels are used for each primer pair, requiring multicolor capabilities.

There is an increasing trend in the application of DNA amplification in forensic identification and genetic screening. The serious implications of many of these tests, however, places extreme requirements for accuracy on the results. During the introductory phase of establishing the utility of amplification technologies, confirmation of results obtained through screening by a second technique will be required. The ultimate confirmation of results obtained through screening DNA amplification products is directly determining the DNA sequence of the sample in question. DNA sequencing, however, is labor intensive and automation of many of the steps involved will be needed for its routine performance outside of basic research laboratories. A capillary based instrument, with automatic gel replacement, coupled with the high throughput system described herein fulfills many of these requirements.

One advantage of introducing DNA to diagnostic assays versus research applications is that, in general, the normal sequence of the amplification product being screened is known. This greatly reduces the demands placed on an automated instrument. It is expected that it will be possible to create reference patterns of DNA sequences within the instrument which would then be automatically compared to the pattern obtained from sequencing a DNA sample selected by screening. The task of recognizing differences in the two patterns is less difficult than calling an unknown sequence. In addition, since essentially the same sequences are examined repetitively, labeled primers can be used which typically results in superior sequencing results compared to other labeling methods.

Homogeneous competitive immunoassay utilizing CE-LIF detections is another applications having potential benefit from the detection system of the present invention. Competitive immunoassay can be generally described by the following equation:

Ag=Antigen in serum sample (digoxin for an example)
Ag*=Labeled antigen synthesized as the probe reagent
AB=Antibody to the antigen (limited amount)

More particularly, and using a digoxin assay as an example of homogeneous competitive immunoassay by CE-LIF, digoxigenin labeled tetramethylrhodamine (fluorescence molecule), using an oligonucleotide as the charge carrier, is used as a species for probing the immunochemical reaction. Addition of an antibody to digoxin results in the formation of Ag*–AB complex. Using an LIF system, there are two species which can be detected, namely, free fluorescently labeled digoxin (Ag*) and antibody bound fluorescently labeled digoxin (Ag*–AB). In clinical environments where numerous samples are analyzed simultaneously, the high throughput characteristic of the present invention can provide decreased analytical time and increased sensitivity.

Advantageously, the present invention is particularly useful in multianalyte immunoassay systems which can be illustrated using Digoxin and theophylline as the model system. Samples containing digoxin (D) and theophylline (T) in biological fluid are competing against fluorescent labeled digoxin (D*) and fluorescent labeled theophylline (T*) with limited amount of antibody to digoxin (Fab) and theophylline (M-Ab). The amount of D* or T* is directly related to the amount of digoxin or theophylline present in the biological fluid. Those skilled in the art will recognize that the detection system of the present invention can provide the high sensitivity and high sample throughput demanded in multi-analyte assays using CE-LIF separation and detection.

The foregoing description of specific embodiments of this invention have been presented for purposes of illustration and description. They are not intended to be exhaustive or to limit the invention to the precise forms disclosed, and many modifications and variations are possible i light of the above teaching. It is intended that the scope of the invention be defined by the claims appended hereto and their equivalents.

What is claimed is:

1. A system for detecting electromagnetic radiation from a plurality of analytical samples, said system comprising:
   a plurality of sample volumes, each of said sample volumes confined within a portion of a capillary column;
   an electromagnetic radiation source;
   a mirror for receiving electromagnetic radiation from the electromagnetic radiation source and for reflecting said electromagnetic radiation to said sample volumes;
   a scanner attached to the mirror;
   a detector for detecting sample electromagnetic radiation from said sample volumes, said sample electromagnetic radiation, generated as a result of interaction of the reflected electromagnetic radiation with said sample.

2. The system of claim 1 wherein said capillary columns form a capillary array comprising a plurality of coplanar side-by-side capillary columns.

3. The system of claim 1 wherein said electromagnetic radiation source is a laser.

4. The system of claim 1 wherein said scanner is a galvo scanner.

5. The system of claim 1 further including a collector means for collecting said sample electromagnetic radiation from said sample volumes, said sample electromagnetic radiation generated as a result of interaction of the reflected electromagnetic radiation with said sample volume.

6. The system of claim 5 wherein said collector means is a parabolic reflector.

7. The system of claim 6 wherein said parabolic reflector includes a first entrance aperture for the reflected electromagnetic radiation to contact each of said sample volumes.

8. The system of claim 1 wherein said detector is selected from the group consisting of photomultiplier tube, charged coupled device, and photodiodes.

9. A system for detecting electromagnetic radiation from a plurality of analytical samples containing fluorescent labels, said system comprising:
   a plurality of sample volumes, each of said sample volumes confined within a portion of a capillary column;
   an excitation radiation source;
   a mirror for receiving said excitation radiation from the excitation radiation source and for reflecting said excitation radiation to said sample volumes;
   a galvo-scanner attached to the mirror;
   collecting means for collecting fluorescence emission, said fluorescence emission generated as a result of said excitation radiation interacting with the fluorescent label; and
   a detector for detecting said fluorescence emission transmitted by said collecting means.

10. The detector system of claim 9 wherein said capillary columns are spatially arranged in a coplanar side-by-side relationship to form a capillary array.

11. The detector system of claim 9 wherein said excitation radiation source is a laser.

12. The detector system of claim 9 wherein said collector means is a parabolic reflector comprising a first aperture for receiving said reflected excitation radiation and a second aperture for transmitting said fluorescence emission, said parabolic reflector position around said capillary array.

13. The detector system of claim 9 further comprising filter means for transmitting excitation radiation of a selected wavelength to said mirror.

14. The detector system of claim 10 further including filter means for transmitting emission radiation of a selected wavelength to said detector.

15. The detector system of claim 9 further comprising a means for blocking scattered electromagnetic radiation scattered by the capillary array.

16. A system for detecting electromagnetic radiation from a plurality of analytical samples containing fluorescent labels, said system comprising:
   a plurality of sample volumes, each of said sample volumes confined within a portion of a capillary column said capillary columns positioned in a coplanar side-by-side relationship to form a capillary array;
   at least one excitation radiation sources;
   a mirror for receiving said excitation radiation from the excitation radiation source and for reflecting said excitation radiation to said sample volumes;
   a galvo-scanner attached to the mirror;
   a parabolic reflector surrounding said capillary array, said parabolic reflector comprising a first aperture for receiving reflected excitation radiation and a second aperture for transmitting fluorescence emission, said fluorescence emission generated as a result of said excitation radiation interacting with the fluorescent label;
   a filter wheel comprising a plurality of filter means, each of said filter means capable of transmitting emission radiation of a selected wavelength; and
   a detector for detecting said fluorescence emission transmitted by said parabolic reflector.

17. The detection system of claim 16 further including a scatter bar placed in a plane orthogonal to an axis of said capillary array.

18. The detection system of claim 16 wherein said detector comprises a photomultiplier tube.

19. The detection system of claim 16 further including computing means for processing signals received from said detector.

20. A method of detecting the presence of samples, each sample contained within a sample volume, said method comprising:

provic a detection system comprising:

a plurality of said sample volumes, each of said sample volumes confined within a portion of a capillary column;

an electromagnetic radiation source;

a mirror for receiving electromagnetic radiation from the electromagnetic radiation source and for reflecting said electromagnetic radiation to said sample volumes;

a scanner attached to the mirror;

a detector for detecting sample electromagnetic radiation from said sample volumes, said sample electromagnetic radiation, generated as a result of interaction of the reflected electromagnetic radiation with said sample;

causing said electromagnetic radiation source to send electromagnetic radiation to said mirror;

causing said scanner to align said mirror so that said electromagnetic radiation is reflected from said mirror and focused on a first sample volume;

detecting sample electromagnetic radiation at said detector, said sample electromagnetic radiation generated as a result of interaction between said reflected electromagnetic radiation and said sample.

21. The method of claim 20 wherein following said detecting step said method further comprises the steps of:

causing said scanner to align said mirror so that said electromagnetic radiation is reflected from said mirror and focused on a second sample volume;

detecting sample electromagnetic radiation at said detector, said sample electromagnetic radiation generated as a result of interaction between said reflected electromagnetic radiation and sample in said second sample volume.

22. The method of claim 20 wherein causing said scanner to align said mirror is sequentially repeated so that said electromagnetic radiation is reflected from said mirror and focused on said sample volumes and said sample electromagnetic radiation is detected, one at a time, in a sequential manner.

23. The method of claim 22 further comprising the step of causing said scanner to align said mirror so that said electromagnetic radiation is reflected from said mirror and focused on said first sample volume.

24. A method of detecting the presence of fluorescence labeled samples, each sample contained within a sample volume, said method comprising:

providing a detection system comprising:

a plurality of said sample volumes, each of said sample volumes confined within a portion of a capillary column, said capillary columns arranged in a coplanar arrangement to form a capillary array;

at least one excitation radiation laser source;

a mirror for receiving excitation radiation from said excitation radiation source and for reflecting said excitation radiation to said sample volumes;

a galvoscanner attached to the mirror;

a parabolic reflector surrounding said capillary array;

a detector for detecting fluorescence emission from said sample volumes, said fluorescence emission, generated as a result of interaction of the reflected excitation radiation with said sample; and a filter wheel comprising a plurality of filter means for transmitting selected wavelengths of emission radiation from said parabolic reflector to said detector;

causing a first laser source to send excitation radiation to said mirror;

causing said galvo scanner to align said mirror so that said excitation radiation is reflected from said mirror and focused on a first sample volume in a first capillary;

detecting emission radiation at said detector, said emission radiation having a first wavelength and generated as a result of interaction between said reflected electromagnetic radiation and said sample;

causing said filter wheel to rotate;

detecting emission radiation at said detector, said emission radiation having a second wavelength and generated as a result of interaction between said reflected electromagnetic radiation and said sample;

causing a second excitation radiation source to send excitation radiation to said mirror; and detecting emission radiation at said detector, said emission radiation having a third wavelength and generated as a result of interaction between said reflected electromagnetic radiation and said sample.

25. A capillary electrophoresis system comprising:

a capillary electrophoresis array;

a first and a second excitation light source for exciting fluorescent labeled samples, wherein the labeled samples include a first, a second, a third and a fourth excitable label, the labeled samples being included within capillaries of the capillary electrophoresis array;

a mirror attached to a scanner for moving a reflected beam from the excitation light source to sequentially illuminate each of the capillaries in the array;

a first filter which exhibits blocking at the wavelength of the first excitation light source and transmittance in the spectral region of a signal emitted from the first excitable label;

a second filter which exhibits blocking at the wavelength of the first excitation light source and transmittance in the spectral region of a signal emitted from the second excitable label;

a third filter which exhibits blocking at the wavelength of the second excitation light source and transmittance in the spectral region of a signal emitted from the third excitable label;

a fourth filter which exhibits blocking at the wavelength of the second excitation light source and transmittance in the spectral region of a signal emitted from the fourth excitable label; and means for receiving a signal from the different capillaries, the signal being generated as a result of interaction of the reflected beam with samples included in the different capillaries.

* * * * *